United States Patent [19]

Dang Vu et al.

[11] 4,268,701

[45] May 19, 1981

[54] PROCESS FOR PRODUCING HIGH OCTANE GASOLINE AND PARTICULARLY LEAD-FREE GASOLINE

[75] Inventors: Quang Dang Vu, Paris; Yves Chauvin, Le Pecq; Jean Gaillard, Lyons; Bernard Torck, Boulogne sur Seine; Michel Hellin, Andresy, all of France

[73] Assignee: Institut Francais du Petrole, Rueil-Malmaison, France

[21] Appl. No.: 75,486

[22] Filed: Sep. 14, 1979

[30] Foreign Application Priority Data

Sep. 14, 1978 [FR] France .................. 78 26644

[51] Int. Cl.$^3$ .................. C07C 2/08; C07C 2/58
[52] U.S. Cl. .................. 585/329; 585/302; 585/331; 585/332

[58] Field of Search ............. 585/14, 302, 321, 331, 585/332

[56] References Cited

U.S. PATENT DOCUMENTS

| | | | |
|---|---|---|---|
| 2,594,343 | 4/1952 | Pines | 585/332 |
| 2,904,498 | 9/1959 | Findlay | 585/302 |
| 3,663,646 | 5/1972 | Chapman | 585/332 |

*Primary Examiner*—Curtis R. Davis
*Attorney, Agent, or Firm*—Millen & White

[57] ABSTRACT

High octane gasoline is obtained from $C_3/C_4$ olefinic cuts by a combination of steps: oligomerization of the $C_3$ fraction, hydroisomerization of 1-butene in the $C_4$ cut, fractionation of the resultant $C_4$ cut, hydrogenation of isobutene and alkylation. Resultant fractions are admixed to produce the desired high octane gasoline.

10 Claims, 1 Drawing Figure

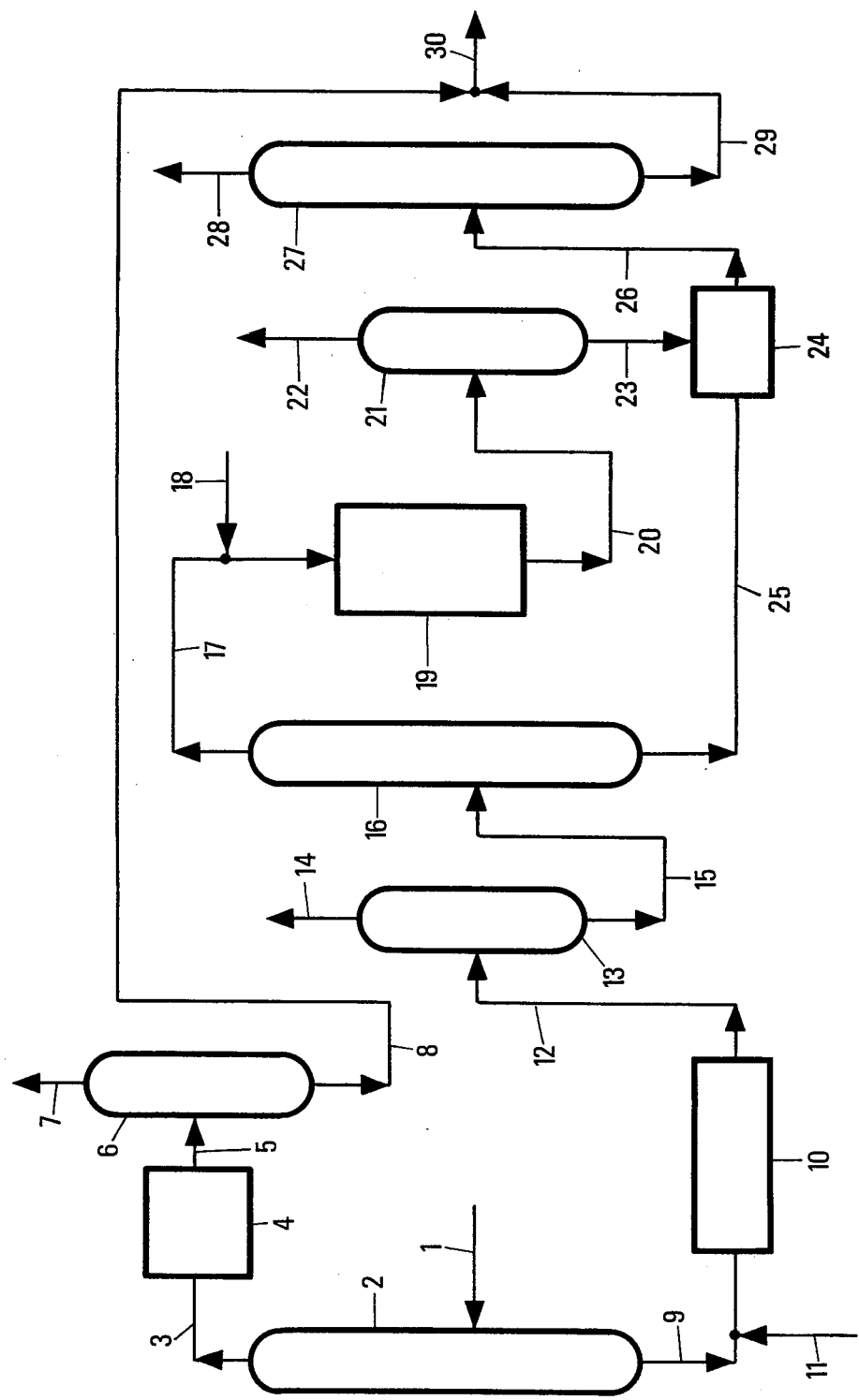

PROCESS FOR PRODUCING HIGH OCTANE GASOLINE AND PARTICULARLY LEAD-FREE GASOLINE

BACKGROUND OF THE INVENTION

This invention concerns a process for producing gasoline of high octane number which can be used without addition of antiknock agents such as tetraethyl lead.

THE PROBLEM

Up to now lead-free gasoline has been produced in the world from the preferred following sources:

High severity catalytic reforming of naphtha, or
Alkylation of olefinic $C_3$–$C_4$ catalytic cracking cuts.

Lead-free gasoline, produced by high severity catalytic reforming is not ideal with respect to pollution and public health. As a matter of fact it contains benzene, whose vapor has proved very toxic.

On the contrary, alkylation yields gasoline which is satisfactory as concerns both the ecological point of view and the purely technical engine problems.

Unhappily this route is now restrained by the isobutane shortage.

More than ever it is necessary to find a process for obtaining valuable products from catalytic cracking $C_3$–$C_4$ cuts, which process is self-sufficient in isobutane and capable of yielding gasoline of equivalent quality.

Since the alkylation reaction between isobutane and a $C_3$ or $C_4$ olefin is equimolecular, it is found that the theoretical amount of isobutane is 1.38 kg for 1 kg of propylene or 1.035 kg for 1 kg of butenes.

It has been observed that the $C_3$–$C_4$ catalytic cracking cuts suffer generally from the drawback of a heavy deficiency as concerns the isobutane content which is far from being sufficient to satisfy the above stoichiometrical conditions. A typical cut has the following composition (% by weight):

$C_3^{==}$ propene: 25.00
$C_3$ propane: 8.35
$iC_4$ isobutane: 23.35
$iC_4^{==}$ isobutene: 10.65
$C_4^{1==}$ n. 1-butene: 6.65
$C_4^{2==}$ n. 2-butene: 18.00
$nC_4$ n-butane: 8.00

It is thus clear that the isobutane proportion is not even one third of the stoichiometrical proportion of olefins.

STATE OF THE ART

The lack of balance of $C_3$–$C_4$ cuts is well known. For example U.S. Pat. No. 3,758,628 proposes to obviate it by using simultaneously a hydrocracking unit and a catalytic cracking unit. But, as shown above, the present trend is towards a stagnation or even a reduction in the number and the capacity of the existing hydrocracking units. Moreover, hydrocracking is an expensive operation which yields a number of products other than isobutane, which products are not always marketable.

THE INVENTION

The present invention resolves the above problem in a new, simple and economical manner; it has for object, instead of finding an additional external source of isobutane, to modify the composition of the $C_3$–$C_4$ cut in such manner that said composition is closer to the stoichiometrical composition in the alkylation reaction of olefins with isobutane.

It has also for object to improve the quality of the alkylate by modifying the composition of the olefins in such a manner that the resulting products have a higher octane number. This is achieved by alkylating $C_4$ olefins enriched with n-butenes and impoverished or made free of propylene and isobutene. As a matter of fact, the alkylates obtained by reacting isobutane with propylene or isobutene have an octane number which is not so high as those obtained by reacting isobutane with n-butenes; Research Octane Number: 92.7 when starting from isobutene, 96.8 and 96.2 respectively when starting from 1-butene and 2-butene and about 90 when starting from propylene, when operating with sulfuric acid as catalyst.

According to the invention, the $C_3/C_4$ hydrocarbon charge, when not available as separate $C_3$ and $C_4$ fractions, is fractionated to a first fraction (A) of high $C_3$ hydrocarbon content, particularly of high propene content, and a second fraction (B) of high $C_4$ hydrocarbon content, particularly of high isobutane, isobutene, 1-butene and 2-butenes content.

The first fraction (A) is oligomerized essentially to $C_6$ olefins. The resultant oligomerizate constitutes the first high octane gasoline fraction (I). The second fraction (B) is hydroisomerized, to convert at least a portion of 1-butene to 2-butene; when butadiene and/or acetylenic hydrocarbons are present, they are also hydrogenated. The hydroisomerization product is fractionated, for example by superfractionation, to a fraction (C) of higher isobutane and isobutene content and a fraction (D) of higher 2-butene content and lower isobutene content. Fraction (C) is then hydrogenated, so as to increase its isobutane content (isobutene is converted to isobutane), yielding fraction (E).

Fraction (E) is reacted with fraction (D) in an alkylation zone, to produce a high octane number alkylate (II). The alkylate (II) may be mixed with the oligomerizate (I) for obtaining a high octane gasoline or gasoline constituent, which can be used without lead, either as such or in admixture with, for example, a reformate or other fractions of the gasoline range.

According to another embodiment, which can be used when starting from a common $C_3$–$C_4$ fraction, this common fraction is subjected to the hydroisomerization of 1-butene, before fractionation to a $C_3$ cut and a $C_4$ cut. In the course of this treatment, the traces of diolefins and acetylenic hydrocarbons are eliminated by hydrogenation. The oligomerization of the so-purified $C_3$ cut is thus made easier.

DETAILED DESCRIPTION OF THE INVENTION

The hydrocarbon charge is, for example, a $C_3$–$C_4$ catalytic cracking cut. It may be available as a $C_3$–$C_4$ mixture and must then be fractionated to a $C_3$ cut and a $C_4$ cut as indicated above; it may also be available in the form of previously separated $C_3$ and $C_4$ fractions, as obtained, for example, by distillation of the effluent from the catalytic cracking unit.

The catalytic cracking may be of any known type, for example, fluid catalytic cracking of a distillate of high saturated hydrocarbon content as obtained, for example, by straight-run distillation of a crude oil. The catalytic cracking processes are well known and a detailed description thereof is unnecessary. The catalysts are, for example, silica-alumina, clay or a zeolite. A detailed description is given, for example in U.S. Pat. No. 3,758,628.

The C₃–C₄ cut usually comprises 0.15 to 0.6 mole of isobutane per mole of olefin. Under this condition, a typical composition by weight is:

| | |
|---|---|
| isobutane | 15 to 30% |
| isobutene | 5 to 15% |
| 2-butenes | 10 to 25% |
| propene | 15 to 35% |
| 1-butene | 3 to 10% |
| propane + butane | 8 to 30% |

When the catalytic cracking product appears as separate C₃ and C₄ cuts, their composition is, for example, by weight:

| | | |
|---|---|---|
| C₃ cut: | propane | 15 to 50% |
| | propylene | 50 to 85% |
| C₄ cut: | n-butane | 5 to 20% |
| | isobutane | 20 to 50% |
| | isobutene | 10 to 25% |
| | 1-butene | 5 to 15% |
| | 2-butene | 10 to 40% |

The fractionation between the C₃ cut and the C₄ cut can be performed easily by distillation. It is not necessary that the fraction C₃ be entirely free from C₄ hydrocarbons or conversely that the C₄ fraction be entirely free of C₃ hydrocarbons.

The oligomerization of the C₃ hydrocarbon cut is preferably performed in the liquid phase by contacting said cut with a catalyst obtained by contacting (or reacting) a compound of a transition metal from groups IV to VIII with a hydrocarbylaluminum compound, preferably a nickel compound with a hydrocarbylaluminum halide, for example a monohydrocarbylaluminum dihalide or a hydrocarbylaluminum sesquichloride. The reaction is conducted in most cases at a temperature from 0° to 60° C., preferably from 30° to 50° C. The nickel compound may be, for example, a carboxylate, an acetylacetonate, a phosphine complex of a nickel salt such as a chloride or an acetylacetonate. The reaction is well known and attention is called, for example, to the following patent specifications: U.S. Pat. Nos. 2,969,408 and 3,655,810; French Pat. No. 1,591,577. The state of the art is illustrated by U.S. Pat. Nos. 3,032,544; 3,390,201; 3,485,881; 3,321,546; 3,482,001 and 3,467,726.

Compounds of other metals than nickel may also be used, such as, for example, compounds of titanium (U.S. Pat. No. 3,686,350), cobalt (U.S. Pat. No. 3,686,353), chromium (U.S. Pat. No. 3,709,954 and 3,726,939), vanadium (U.S. Pat. No. 3,737,476), tungsten (U.S. Pat. No. 3,784,629), etc.

Preference is given to the combination of a nickel compound with a dichloroalkylaluminum; in view of its better selectivity for forming olefins with 6 carbon atoms.

When the oligomerization has been completed, there is obtained an oligomerizate (I) which constitutes one of the desired gasoline fractions.

Other oligomerization techniques may be used, for example, treatment with a catalyst of silica-alumina, phosphoric acid, boron trifluoride, aluminum trichloride, etc. The results are however less satisfactory as concerns the composition of the oligomerizate which contains a greater proportion of heavier oligomers having 9, 12 and 15 carbon atoms; moreover the catalyst cannot be handled easily, it must be changed frequently and finally a relatively high pressure is necessary. The state of the art comprises, for example, the U.S. Pat. Nos. 3,769,363, 3,833,678, 3,758,627 and 3,887,634.

Hydroisomerization of the C₄ cut is necessary to the further fractionation of the C₄ hydrocarbons by distillation. As a matter of fact, 1-butene cannot be separated easily from isobutane, whereas the separation between 2-butene and isobutane is relatively easier. This isomerization is preferably effected by contacting a mixture of the C₄ cut with hydrogen with a supported group VIII noble metal catalyst. The noble metal is preferably palladium (content: 0.01 to 2% by weight) and the preferred carrier is alumina. Other, less preferred, carriers are silica-alumina and carbon. The selectivity of these catalysts may be increased by addition of sulfur or ammonia compounds, or by addition of carbon monoxide, in low proportion, to the hydrocarbon charge or to the catalyst. A preferred technique is that described in U.S. Pat. No. 4,132,745. It consists of pretreating the catalyst with a sulfur compound and then passing hydrogen over the sulfurized catalyst. The state of the art is illustrated, for example, by U.S. Pat. Nos. 3,531,545, 3,772,400, 3,764,633, 3,702,876 and 3,485,887.

The hydroisomerization temperature is usually from 50° to 250° C., preferably from 60° to 140° C. The lowest temperatures are more favorable since they displace the equilibrium in favor of 2-butene. Liquid phase operation is preferred. The pressure is preferably from 5 to 30 atmospheres, said pressure being applied by means of hydrogen either pure or diluted with an inert gas. The hydrocarbon feed rate, calculated as 1-butene, is usually from 1 to 50, preferably 5 to 20 liters (in the liquid state) per liter of catalyst per hour. For example, 1 to 15 moles % of hydrogen may be used, with respect to 1-butene.

Other techniques for isomerizing 1-butene to 2-butene may be used, although they are not so advantageous as concerns the overall yield of the process and the quality of the resultant products.

When isomerization has been completed, the hydrocarbons are fractionated to a fraction (C) of increased isobutane and isobutene content and a fraction (D) of increased 2-butene content. This fractionation may be effected by distillation, in particular according to the super-fractionation technique. One or, for example, two columns may be used with, for example, 50 to 200 theoretical plates. Thorough fractionation is not necessary. This technique is well known and no further description appears necessary.

Other fractionation techniques may be used, although they are not so advantageous, for example fractionation with molecular sieves, for example a 5 Å molecular sieve.

Fraction (C) of increased isobutane and isobutene content is then subjected to hydrogenation to increase the isobutane content. The hydrogenation rate is preferably so selected that the isobutane content is raised to a value adapted to the further alkylation reaction; this value is theoretically 1 mole isobutane per mole of monoolefin, although another value may be selected for other reasons.

The hydrogenation is effected by passing a mixture of the fraction (C) with hydrogen in contact with a catalyst suitable for hydrogenating mono-olefins to saturated hydrocarbons. This catalyst may be a group VIII noble metal catalyst, for example platinum or palladium, or a group VIII non-noble metal catalyst, for example nickel, or a catalyst comprising both an element from group VI A (tungsten, molybdenum) and an element from the iron group (nickel, cobalt, iron). A carrier may be used. This type of hydrogenation is well known and a further description is not necessary. The temperature depends on the catalyst and usually ranges from 50° to 400° C. Fraction (E) as above defined is thus obtained.

Fraction (E) is reacted with fraction (D) under aliphatic alkylation conditions.

The known catalysts for the reaction of isobutane with butenes may be used, hydrofluoric acid being preferred. Other catalysts are sulfuric acid and Friedel and Crafts catalysts.

As state of the art, the following U.S. Pat. Nos. are mentioned: 2,308,560; 2,320,199; 2,429,205; 2,768,987; 2,818,458; 2,914,592; 2,920,124 and 3,855,344, among others.

The invention is by no way limited to particular conditions of the well known alkylation reaction. An alkylate (II) is thus obtained, which constitutes a second gasoline fraction of high octane number and can be admixed with the oligomerizate (I). The resultant mixture constitutes a lead-free gasoline or a constituent thereof. Preferably at least 90% of the final gasoline distils over 40° C. and below 220° C.

The invention is illustrated by the accompanying drawing.

A catalytic cracking effluent (line 1), or preferably a $C_3$-$C_4$ fraction from said effluent, is fractionated in a distillation unit diagrammatically shown as column 2, into a $C_3$ fraction and a $C_4$ fraction. The $C_3$ fraction is fed, through line 3, to the oligomerization unit 4. The effluent from said unit is fed, through duct 5, to column 6 for fractionation. The light hydrocarbons are separated through line 7; they can be recycled to unit 4. An oligomerization gasoline fraction is discharged through line 8. Its distillation range is between about 40° and 220° C., but it mainly contains propylene dimers. This fraction is fed to the gasoline "pool".

The $C_4$ fraction, discharged through line 9, is supplied to the hydroisomerization reactor 10, after admixture with hydrogen (duct 11). The outflow is fed through duct 12 to the separator 13. The gas is discharged through line 14 and the $C_4$ hydrocarbon liquid phase is fed, through duct 15, to the super-fractionation unit 16.

A fraction of increased isobutane and isobutene content is recovered from the top through line 17; it is admixed with hydrogen (line 18) and fed to the hydrogenation reactor 19. The outflow is fed, through duct 20, to the separator 21. Hydrogen is discharged from the top (line 22) and may be recycled. The $C_4$ hydrocarbon effluent of increased isobutane content is fed, through line 23, to the alkylation reactor 24.

The latter also receives, through duct 25, the fraction of increased butane and 2-butene content, as recovered from the super-fractionation step. The alkylation product is fed, through duct 26, to the stabilization column 27: the unconverted $C_4$ hydrocarbons are discharged through duct 28; the alkylate (II) is discharged from the bottom through duct 29. It can be admixed with the oligomerizate from line 8 to obtain a gasoline of high octane number in line 30.

The above schema comprises distinct stabilization columns for the alkylate and the oligomerizate. The alkylate and the oligomerizate may also be mixed before stabilization and the resultant mixture stabilized thereafter.

EXAMPLE

The composition of the charge and the resultant fractions is given in the Table below. The operation was in conformity with the flow sheet of the accompanying drawing.

The operating conditions were as follows: the $C_3$ and $C_4$ hydrocarbons were first separated by distillation.

The oligomerization unit was operated with a catalyst of nickel octoate and dichloroethylaluminum in the atomic ratio Al/Ni of 15:1, at a concentration of 20 parts per million of parts by weight of nickel, at a temperature of 40°–45° C., at sufficient pressure to maintain propylene and propane in the liquid phase (about 10 bars) and with an average residence time of 3 hours.

The catalyst, when discharged from the reactor, was first neutralized with anhydrous ammonia and then washed with water to eliminate the catalyst residues. The effluent was then fed to a stabilization column for recovering unreacted propane and propylene, at the top, and stabilized gasoline, at the bottom.

Hydroisomerization was conducted at 80°–110° C. under 30 atmospheres. The catalyst comprised 0.3% Pd on alumina; it was pre-treated with hydrogen sulfide and then with hydrogen, as described in the U.S. Pat. No. 4,132,745.

Super-fractionation was performed in two columns of 80 plates each.

Hydrogenation of isobutene was effected in a hydrogen atmosphere at about 100° C. with a catalyst of 0.3% palladium on alumina, at a hydrocarbon hourly feed rate of 3 volumes per volume of catalyst and under a total pressure of 30 bars.

Alkylation was performed in the presence of 85.9% hydrofluoric acid at a temperature from 27° to 38° C., a total pressure of 14 bars and an isobutane/olefins ratio of 6/1 by weight, in a reactor where the two phases (hydrocarbons and hydrofluoric acid) flow countercurrently. The isobutane/olefin ratio of 6, necessary for a high alkylation selectivity is obtained by recycling isobutane. The effluent is fractionated, after passage in a settler to recover the alkylate and the isobutane to be recycled.

The resultant lead-free alkylate oligomerizate mixture has a research octane number (RON) of 98, while the alkylate and the oligomerizate have each separately a RON of 96.5. The RON of 98 results from the very high RON value as mixture component of the oligomerizate of about 101 to 102. The MON (Motor Octane Number) of the mixture is 91, while the alkylate MON and the oligomerizate MON are respectively 94 and 82. Here again the MON value as mixture component of the oligomerizate is higher than the MON of the pure oligomerizate.

It must be noted that the omission of isobutene removal from the alkylation feed charge would result in a RON of the alkylate of only 93 and a RON lower than 96 for the final mixture. Moreover the isobutane proportion of the cut would be insufficient to alkylate all the butenes.

The final mixture having a specific gravity of 0.704 constitutes a light gasoline. Its initial distillation point is 40° C.; 10% distill at 60° C., 50% at 92° C. and 90% at 118° C.; the final point being 188° C.

The operation was repeated, while using a charge of $C_3/C_4$ coking cut, instead of a $C_3/C_4$ catalytic cracking cut. Provided the composition is the same or similar, the results are substantially unchanged.

| | COMPOSITION (WEIGHT PER TIME UNIT) | | | | | | | | | |
|---|---|---|---|---|---|---|---|---|---|---|
| | Initial charge (line 1) | C$_3$ cut (line 3) | C$_4$ cut (line 9) | Stabilized oligomerizate (line 8) | Hydroisomerizate (line 15) | Iso fraction (line 17) | Normal fraction (line 25) | Hydrogenated iso fraction (line 23) | Stabilized alkylate (line 29) | Total gasoline (line 30) |
| Propylene | 15.0 | 15.0 | | | | | | | | |
| Propane | 5.0 | 5.0 | | | | | | | | |
| Isobutane | 14.0 | | 14.0 | | 14.0 | 14.0 | | 18.0 | | |
| Isobutene | 6.4 | | 6.4 | | 6.4 | 6.3 | 0.1 | 2.4 | | |
| 1-butene | 4.0 | | 4.0 | | 0.6 | 0.5 | 0.1 | 0.2 | | |
| 2-butenes | 10.8 | | 10.8 | | 14.2 | | 14.2 | | | |
| n-butane | 4.8 | | 4.8 | | 4.8 | 0.6 | 4.2 | 0.9 | | |
| Gasoline (40°–188° C.) | | | | 14.8 | | | | | 34.6 | 49.4 |

What is claimed is:

1. A process for producing a blended high octane gasoline, which comprises the steps of:
    (a) oligomerizing an olefinic C$_3$ hydrocarbon cut comprising propylene, and recovering an oligomerizate boiling in the gasoline range;
    (b) hydroisomerizing an olefinic C$_4$ hydrocarbon cut comprising isobutene, isobutane, 1-butene and 2-butene under 1-butene isomerizing conditions, and recovering an isomerized C$_4$ cut having an increased proportion of 2-butene and a decreased proportion of 1-butene relative to said olefinic C$_4$ hydrocarbon cut;
    (c) fractionating the isomerized C$_4$ cut from step (b) and separately recovering a first fraction having an increased proportion of isobutene and isobutane relative to said isomerized C$_4$ cut, and a second fraction having an increased proportion of 2-butene relative to said isomerized C$_4$ cut;
    (d) hydrogenating said first fraction from step (c) under isobutene hydrogenating conditions, and recovering an effluent having an increased proportion of isobutane relative to said first fraction;
    (e) admixing the effluent from step (d) and said second fraction from step (c), subjecting the resultant mixture to hydrocarbon alkylation conditions, and recovering an alkylate boiling in the gasoline range; and
    (f) blending at least a portion of the oligomerizate from step (a) with at least a portion of the alkylate from step (e) to produce a blended high octane gasoline.

2. A process according to claim 1, wherein the C$_3$ cut used in step (a) and the C$_4$ cut used in step (b) are each produced by fractional distillation of a C$_3$/C$_4$ catalytic cracking cut.

3. A process according to claim 1, wherein the oligomerization in step (a) is effected in the presence of a catalyst obtained by contacting a group IV to VIII metal compound with an alkylaluminum compound.

4. A process according to claim 3, wherein the metal compound is a nickel compound and the alkylaluminum compound is a hydrocarbyl aluminum halide.

5. A process according to claim 1, wherein the hydroisomerization in step (b) is effected in the presence of a supported group VIII noble metal catalyst.

6. A process according to claim 5, wherein the catalyst is palladium on alumina, the catalyst being presulfided and then treated with hydrogen.

7. A process according to claim 2, wherein said C$_3$/C$_4$ catalytic cracking cut has the following composition by weight:
    propylene: 15–35%
    isobutane: 15–30%
    isobutene: 5–15%
    1-butene: 3–10%
    2-butenes: 10–25%
    propane+n-butane: 8–30%

8. A process according to claim 1, wherein the alkylation in step (e) is effected in the presence of a catalyst comprising hydrofluoric acid.

9. A process according to claim 8, wherein the C$_3$ cut used in step (a) and the C$_4$ cut used in step (b) have the following respective compositions by weight:

| C$_3$ cut | | C$_4$ cut | |
|---|---|---|---|
| propane | 15–50% | n-butane | 5–20% |
| propylene | 50–85% | isobutane | 20–50% |
| | | isobutene | 10–25% |
| | | 1-butenes | 5–15% |
| | | 2-butenes | 10–40% |

10. A process according to claim 2, wherein said C$_3$/C$_4$ catalytic cracking cut is subjected to hydroisomerisation under 1-butene isomerization conditions and then fractionally distilled to produce C$_3$ and C$_4$ cuts; whereby the oligomerization of the resultant C$_3$ cut is made easier.

* * * * *